US006939676B2

(12) United States Patent
Burke et al.

(10) Patent No.: US 6,939,676 B2
(45) Date of Patent: Sep. 6, 2005

(54) SELECTION PROCEDURE FOR IDENTIFYING TRANSGENIC CELLS, EMBRYOS, AND PLANTS WITHOUT THE USE OF ANTIBIOTICS

(75) Inventors: John J. Burke, Lubbock, TX (US); Patrick J. O'Mahony, Rathfarnam (IE); Jeffrey P. Velten, Lubbock, TX (US); Melvin J. Oliver, Lubbock, TX (US)

(73) Assignee: The United States of America as represented by the Secretary of Argriculture, Washington, DC (US)

( * ) Notice: Subject to any disclaimer, the term of this patent is extended or adjusted under 35 U.S.C. 154(b) by 61 days.

(21) Appl. No.: 10/331,861

(22) Filed: Dec. 30, 2002

(65) Prior Publication Data

US 2004/0126768 A1 Jul. 1, 2004

(51) Int. Cl.$^7$ .......................... C12Q 1/68; C12N 15/63; C12N 15/82; C12N 15/74; C12N 15/09; A01H 1/00
(52) U.S. Cl. ......................... 435/6; 435/455; 435/468; 435/471; 435/320.1; 800/278; 800/289
(58) Field of Search ........................... 435/6, 455, 468, 435/471, 320.1; 800/278, 289

(56) References Cited

U.S. PATENT DOCUMENTS

| | | |
|---|---|---|
| 5,296,462 A | 3/1994 | Thomashow |
| 5,756,343 A | 5/1998 | Wu et al. |
| 5,827,685 A | 10/1998 | Lindquist |
| 5,891,859 A | 4/1999 | Thomashow |
| 5,922,929 A | 7/1999 | Zimmerman et al. |

OTHER PUBLICATIONS

Gilmour, S.J., et al., "Overexpression of the *Arabidopsis* CBF3 Transcriptional Activator Mimics Multiple Biochemical Changes Associated with Cold Acclimation", 2000, Plant Phys., vol. 124: pp. 1854–1865.*
Somkuti, G.A. et al., "Structural and Functional Properties of the hsp 16.4–Bearing Plasmid pER341 in *Streptococcus thermophilus*", 1998, Plasmid, vol. 40: pp. 61–72.*
Wells, D.R., et al. "HSP101 functions as a specific translational regulatory protein whose activity is regulated by nutrient status", 1998, Genes & Dev., vol. 12: pp. 3236–3251.*
Prandl, R.. et al., "HSF3, a new heat shock factor from *Arabadopsis thaliana*, derepresses the heat shock response and confers thermotolerance when overexpressed in transgenic plants", 1998, Mol. Gen. Genetics, vol. 258:, pp. 269–278.*

* cited by examiner

*Primary Examiner*—David Guzo
*Assistant Examiner*—Michael Burkhart
(74) *Attorney, Agent, or Firm*—John D. Fado; Randall E. Deck; Lesley Shaw

(57) ABSTRACT

Transgenic cells may be selected using temperature sensitive marker proteins. In this method, a population of host cells are transformed with a foreign DNA construct which includes at least one first nucleic acid coding sequence and a second nucleic acid sequence encoding a temperature sensitive marker protein, wherein each of the first and second nucleic acid coding sequences are operatively linked to gene expression control sequences. Suitable temperature sensitive marker proteins which may be used herein include heat shock proteins, heat shock transcription factors, cold regulated proteins (COR), or cold regulated protein transcription factors. Following transformation, the population of cells are cultured under temperature conditions wherein growth of non-transformed cells is suppressed or prevented while growth of cells transformed with the DNA construct is supported or promoted. Thus, survival and/or significant growth of a cell is an indication that the cell has been successfully transformed with the DNA construct. Those cells are considered presumptively positive transformants, and may be recovered.

20 Claims, 3 Drawing Sheets

SELECTION PROCEDURE FOR IDENTIFYING TRANSGENIC CELLS, EMBRYOS, AND PLANTS WITHOUT THE USE OF ANTIBIOTICS

BACKGROUND OF THE INVENTION

1. Field of the Invention

The invention relates to a novel system and method utilizing temperature sensitive markers for identifying and selecting transgenic cells, embryos, and plants.

2. Description of the Prior Art

The DNA constructs of the invention can be used to transform any type of plant cells (see below). A genetic marker must be used for selecting transformed plant cells ("a selection marker"). Selection markers typically allow transformed cells to be recovered by negative selection (i.e., inhibiting growth of cells that do not contain the selection marker) or by screening for a product encoded by the selection marker.

The most commonly used selectable marker gene for plant transformation is the neomycin phosphotransferase II (nptII) gene, isolated from Tn5, which, when placed under the control of plant expression control signals, confers resistance to kanamycin. Fraley et al., 1983, *Proc. Natl. Acad. Sci. USA*, 80:4803. Another commonly used selectable marker gene is the hygromycin phosphotransferase gene which confers resistance to the antibiotic hygromycin. Vanden Elzen et al., 1985, *Plant Mol. Biol.*, 5:299.

Additional selectable marker genes of bacterial origin that confer resistance to antibiotics include gentamycin acetyl transferase, streptomycin phosphotransferase, aminoglycoside-3'-adenyl transferase, and the bleomycin resistance determinant. Hayford et al., 1988, *Plant Physiol.*, 86:1216, Jones et al., 1987, *Mol. Gen. Genet.*, 210:86, Svab et al., 1990, *Plant Mol. Biol.*, 14:197, Hille et al., 1986, *Plant Mol. Biol.*, 7:171. Other selectable marker genes confer resistance to herbicides such as glyphosate, glufosinate or bromoxynil. Comai et al., 1985, *Nature*, 317:741–744, Stalker et al., 1988, *Science*, 242:419–423, Hinchee et al., 1988, *Bio/Technology*, 6:915–922, Stalker et al., 1988, *J. Biol. Chem.*, 263:6310–6314, and Gordon-Kamm et al., 1990, *Plant Cell*, 2:603–618. Other marker genes that have been used include conditional cytotoxic genes, i.e. thymidine kinase that converts ganciclovir (an antiherpic drug) to a toxic compound (Czako and Marton, 1994, Plant Physiol., 104:1067–1071), as well as the pehA gene from *Burkholderia caryophilli* that codes for a phosphonate monoester hydrolase that converts glyceryl glyphosate to the herbicide glyphosate (Dotson et al., 1996, 10:383–392).

Other selectable marker genes for plant transformation are not of bacterial origin. These genes include, for example, mouse dihydrofolate reductase, plant 5-enolpyruvylshikimate-3-phosphate synthase, and plant acetolactate synthase. Eichholtz et al., 1987, *Somatic Cell Mol. Genet.*, 13:67, Shah et al., 1986, *Science*, 233:478, Charest et al., 1990, *Plant Cell Rep.*, 8:643, EP 154,204.

Commonly used genes for screening presumptively transformed cells include β-glucuronidase (GUS), β-galactosidase, luciferase, and chloramphenicol acetyltransferase. Jefferson, R. A., 1987, *Plant Mol. Biol. Rep.*, 5:387., Teeri et al., 1989, *EMBO J.*, 8:343, Koncz et al., 1987, *Proc. Natl. Acad. Sci. USA*, 84:131, De Block et al., 1984, *EMBO J.*, 3:1681, green fluorescent protein (GFP) (Chalfie et al., 1994, *Science*, 263:802, Haseloff et al., 1995, *TIG*, 11:328–329 and PCT application WO 97/41228). Another approach to the identification of relatively rare transformation events has been use of a gene that encodes a dominant constitutive regulator of the *Zea mays* anthocyanin pigmentation pathway. Ludwig et al., 1990, *Science*, 247:449.

SUMMARY OF THE INVENTION

We have now developed a method for the temperature selection of transgenic cells. In this method, a population of host cells is transformed with a foreign DNA construct which includes at least one first nucleic acid coding sequence and a second nucleic acid sequence encoding a temperature sensitive marker protein, wherein each of the first and second nucleic acid coding sequences are operatively linked to gene expression control sequences. Suitable temperature sensitive marker proteins which may be used herein include heat shock proteins, heat shock transcription factors, cold regulated proteins (COR), or cold regulated protein transcription factors. Following transformation, the population of cells are cultured under temperature conditions wherein growth of non-transformed cells is suppressed or prevented while growth of cells transformed with the DNA construct is supported or promoted. Thus, survival and/or significant growth of a cell is an indication that the cell has been successfully transformed with the DNA construct. Those cells are considered presumptively positive transformants, and may be recovered.

In accordance with this discovery, it is an object of this invention to provide a method for the temperature selection of transgenic cells.

Another object of this invention is to provide a method for the selection of transgenic cells by use of selectable marker genes which confer increased thermotolerance.

Still another object of this invention is to provide an alternative method for the selection of transgenic cells which does not require the use of antibiotic resistance or pesticide (including herbicide) resistance markers.

Yet another object of this invention is to provide an alternative method for the selection of transgenic cells which does not require the use of antibiotics, herbicides or other pesticides, or other toxic chemicals in culture media.

Other objects and advantages of this invention will become readily apparent from the ensuing description.

DEFINITIONS

Figure 1:
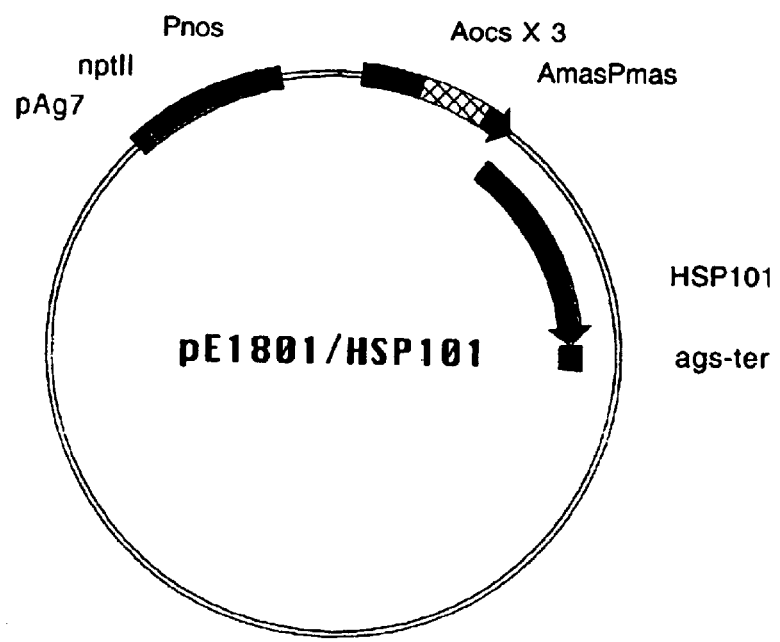
FIG. 1: Diagram of pE1801-ocs/mas 'superpromoter'-HSP101 plasmid.

The following terms are employed herein:

Cloning. The selection and propagation of (a) genetic material from a single individual, (b) a vector containing one gene or gene fragment, or (c) a single organism containing one such gene or gene fragment.

Cloning Vector. A plasmid, virus, retrovirus, bacteriophage, cosmid, artificial chromosome (bacterial or yeast), or nucleic acid sequence which is able to replicate in a host cell, characterized by one or a small number of restriction endonuclease recognition sites at which the sequence may be cut in a predetermined fashion, and which may contain an optional marker suitable for use in the identification of transformed cells, e.g., tetracycline resistance or ampicillin resistance. A cloning vector may or may not possess the features necessary for it to operate as an expression vector.

Codon. A DNA sequence of three nucleotides (a triplet) which codes (through mRNA) for an amino acid, a translational start signal, or a translational termination signal. For example, the nucleotide triplets TTA, TTG, CTT, CTC, CTA, and CTG encode for the amino acid leucine, while TAG, TAA, and TGA are translational stop signals, and ATG is a translational start signal.

DNA Coding Sequence. A DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences and cDNA from eukaryotic mRNA. A polyadenylation signal and transcription termination sequence will usually be located 3' to the coding sequence.

DNA Construct. Artificially constructed (i.e., non-naturally occurring) DNA molecules useful for introducing DNA into host cells, including chimeric genes, expression cassettes, and vectors.

DNA Sequence. A linear series of nucleotides connected one to the other by phosphodiester bonds between the 3' and 5' carbons of adjacent pentoses.

Expression. The process undergone by a structural gene to produce a polypeptide. Expression requires transcription of DNA, post-transcriptional modification of the initial RNA transcript, and translation of RNA.

Expression Cassette. A nucleic acid sequence within a vector which is to be transcribed, and a promoter to direct the transcription. The expression cassette may contain one or more unrelated DNA sequences encoding one or more peptides of interest.

Expression Control Sequence. Expression control sequences are DNA sequences involved in any way in the control of transcription or translation and must include a promoter. Suitable expression control sequences and methods of making and using them are well known in the art.

Expression Vector. A replicon such as a plasmid, virus, retrovirus, bacteriophage, cosmid, artificial chromosome (bacterial or yeast), or nucleic acid sequence which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

Fusion Protein. A protein produced when two heterologous genes or fragments thereof coding for two different proteins not found fused together in nature are fused together in an expression vector. For the fusion protein to correspond to the separate proteins, the separate DNA sequences must be fused together in correct translational reading frame.

Gene. A segment of DNA which encodes a specific protein or polypeptide, or RNA.

Genome. The entire DNA of an organism. It includes, among other things, the structural genes encoding for the polypeptides of the substance, as well as operator, promoter and ribosome binding and interaction sequences.

Heterologous DNA. A DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

Hybridization. The pairing together or annealing of single stranded regions of nucleic acids to form double-stranded molecules.

Nucleotide. A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C"), and thymine ("T"). The four RNA bases are A, G, C, and uracil ("U").

Operably Encodes or Associated. Operably encodes or operably associated each refer to the functional linkage between a promoter and nucleic acid sequence, wherein the promoter initiates transcription of RNA corresponding to the DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

Phage or Bacteriophage. Bacterial virus many of which include DNA sequences encapsidated in a protein envelope or coat ("capsid"). In a unicellular organism a phage may be introduced by a process called transfection.

Plant. Plant refers to a unicellular organism or a multicellular differentiated organism capable of photosynthesis, including algae, angiosperms (monocots and dicots), gymnosperms (ginko, cycads, gnetophytes, and conifers), bryophytes, ferns and fern allies. Plant parts are parts of multicellular differentiated plants and include seeds, pollen, embryos, flowers, fruits, shoots, leaves, roots, stems, explants, etc.

Plant Cell. Plant cell refers to the structural and physiological unit of multicellular plants. Thus, the term plant cell refers to any cell that is a plant or is part of, or derived from, a plant. Some examples of cells encompassed by the present invention include differentiated cells that are part of a living plant, differentiated cells in culture, undifferentiated cells in culture, and the cells of undifferentiated tissue such as callus or tumors.

Plasmid. A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. A cell transformed by a plasmid is called a "transformant."

Polypeptide. A linear series of amino acids connected one to the other by peptide bonds between the alpha-amino and carboxy groups of adjacent amino acids.

Promoter. A DNA sequence within a larger DNA sequence defining a site to which RNA polymerase may bind and initiate transcription. A promoter may include optional distal enhancer or repressor elements. The promoter may be either homologous, i.e., occurring naturally to direct the expression of the desired nucleic acid, or heterologous, i.e., occurring naturally to direct the expression of a nucleic acid derived from a gene other than the desired nucleic acid. A promoter may be constitutive or inducible.

Reading Frame. The grouping of codons during translation of mRNA into amino acid sequences. During translation the proper reading frame must be maintained. For example, the DNA sequence may be translated via mRNA into three reading frames, each of which affords a different amino acid sequence.

Recombinant DNA Molecule. A hybrid DNA sequence comprising at least two DNA sequences, the first sequence not normally being found together in nature with the second.

Ribosomal Binding Site. A nucleotide sequence of mRNA, coded for by a DNA sequence, to which ribosomes bind so that translation may be initiated. A ribosomal binding site is required for efficient translation to occur. The DNA sequence coding for a ribosomal binding site is positioned on a larger DNA sequence downstream of a promoter and upstream from a translational start sequence.

Replicon. Any genetic element (e.g., plasmid, chromosome, virus) that functions as an autonomous unit of DNA replication in vivo, i.e., capable of replication under its own control.

Start Codon. Also called the initiation codon, is the first mRNA triplet to be translated during protein or peptide synthesis and immediately precedes the structural gene being translated. The start codon is usually AUG, but may sometimes also be GUG.

Structural Gene. A DNA sequence which encodes through its template or messenger RNA (mRNA) a sequence of amino acids characteristic of a specific polypeptide.

Transform. To change in a heritable manner the characteristics of a host cell in response to DNA foreign to that cell. An exogenous DNA has been introduced inside the cell wall or protoplast. Exogenous DNA may or may not be integrated (covalently linked) to chromosomal DNA making up the genome of the cell. In prokaryotes and yeast, for example, the exogenous DNA may be maintained on an episomal element such as a plasmid. With respect to eucaryotic cells, a stably transformed cell is one in which the exogenous DNA has been integrated into a chromosome so that it is inherited by daughter cells through chromosome replication. This stability is demonstrated by the ability of the eucaryotic cell to establish cell lines or clones comprised of a population of daughter cells containing the exogenous DNA.

Transcription. The process of producing mRNA from a structural gene.

Translation. The process of producing a polypeptide from mRNA.

DETAILED DESCRIPTION OF THE INVENTION

Traditionally, the production of transgenic cells requires constructing a suitable expression vector or construct containing the desired nucleic acid sequence or gene, introducing the construct into a population of host cells (i.e., transfecting the host cells with the construct), selecting only those transformed cells into which the desired sequence or gene has been successfully introduced, and propagating the selected cells. Because it is usually difficult to differentiate between those cells which have incorporated the desired sequence or gene and those cells which have not, the selection of successful transformants is typically effected by providing marker genes on the construct. By choosing marker genes whose expression can be easily detected during culture, the presence or absence of expression of the selectable marker gene can therefore be used as an index for the successful transformation with the desired sequence or gene.

As mentioned hereinabove, conventional markers in use include genes conferring resistance to antibiotics, herbicides or other pesticides, genes that encode proteins that alter the metabolism of the cell to generate a toxin, and genes encoding enzymes which produce a detectable product or pigment. However, in a departure from established practice, we have discovered that the selection of cells which have been successfully transformed with a DNA construct of interest may be practiced using as a marker a nucleic acid sequence encoding a temperature sensitive marker protein.

A variety of temperature sensitive marker proteins are suitable for use herein, including heat shock proteins (HSP), heat shock transcription factors (HSTF, also referred to as heat shock factors, HSF), cold regulated proteins (COR, also referred to as cold shock proteins), or cold regulated protein transcription factors. The temperature sensitive marker protein selected may be of eukaryotic (animal, plant, or protist) or prokaryotic origin, and may be from the same or different species as the host cell of interest. Moreover, when using heat shock proteins or cold regulated proteins as the marker, the proteins may be cognate (i.e., expressed in normal cells in the absence of temperature stress) or inducible (i.e., produced in normal cells in response to temperature stress). However, use of inducible heat shock proteins or cold regulated proteins is preferred. As will be discussed in greater detail hereinbelow, the selection of a cognate or inducible protein is distinct from the selection of the promoter(s) in the construct.

Without being limited thereto, suitable heat shock proteins which may be used as markers herein include those in the families HSP 100 or 110 (this family has been referred to by different authors as HSP 100 or HSP 110, but each refer to those HSPs having a molecular weight range between approximately 100 and 110 kDa), HSP 90 (HSPs ranging in size between approximately 80 to 94 kDa), HSP 70, HSP 60, and low molecular weight (LMW) HSPs (recognized in the art as those having a molecular weight between 15 and 30 kDa). Numerous heat shock proteins within these families and their corresponding nucleic acid coding sequences have been isolated and described, for example, by Schoffl et al. (1998, *Plant Physiol.*, 117:1135–1141), Schoffl et al. (*Molecular Responses to Heat Stress. IN: Molecular Responses to Cold, Drought, Heat, and Salt Stress in Higher Plants*, R. G. Landes publisher, 1999, pp. 81–88), Vierling (1991, *Annu. Rev. Plant Physiology Plant Mol. Biol.*, 42:579–620), Nover (1997, *Cellular and Molecular Life Sciences*, 53:80–103), Lindquist (U.S. Pat. No. 5,827,685), and Zimmerman et al. (U.S. Pat. No. 5,922,929), and any one of these HSPs may be suitable for use herein. By way of example, preferred heat shock proteins (and the nucleic acid sequences which encode them) for use herein include *Arabidopsis thaliana* heat shock protein 101 (Queitsch et al., 2000, *The Plant Cell*, 12:479–492), and carrot HSP 17.7 (Zimmerman et al., U.S. Pat. No. 5,922,929). A variety of heat shock transcription factors, cold regulated proteins, or cold regulated protein transcription factors, and their corresponding nucleic acid coding sequences, have also been described that are suitable for use herein as temperature sensitive markers, and include but are not limited to the heat shock transcription factors disclosed by Wu et al. (U.S. Pat.

No. 5,756,343), the cold regulation proteins disclosed by Thomashow (U.S. Pat. Nos. 5,296,462 and 5,356,816), and cold regulation protein transcription factors disclosed by Thomashow et al. (U.S. Pat. Nos. 5,891,859, 5,892,009, 5,965,705, and 5,929,305). The contents of each of the publications and patents referred to hereinabove are incorporated by reference herein.

In use, the incorporation of the nucleic acid sequence encoding the temperature sensitive marker protein into the DNA construct will enable those host cells that have been successfully transformed to grow under conditions of extreme temperature, at a significantly greater rate than those cells in the population that were not successfully transformed. If the host cell lacks or possesses a defective native (i.e., normally present and not introduced through the DNA construct) temperature stress response system (heat shock proteins and/or cold regulation proteins) that can be induced upon exposure to the particular temperature extreme used herein, the selection process may be conducted in a single culture step. After their transformation the population of cells (that will include a mix of successfully transformed cells and non-transformed cells) may be subjected to culture under conditions and at an extreme temperature wherein the temperature sensitive marker proteins are expressed and subsequently protect the transformed cells and allow their growth, while the growth of any non-transformed cells is prevented or significantly inhibited. The cells may be cultured on any appropriate growth media, although solid phase media are preferred. The level of inhibition must be sufficient that the successfully transformed cells may be distinguished from the non-transformed cells (i.e., the inhibition must be statistically significant). Thus, successfully transformed cells may be differentiated by exhibition of significantly greater growth as evidenced by size or the production of growth products using techniques known in the art. The precise temperature and culture conditions will vary with the particular host cell, temperature sensitive marker protein, and gene expression control sequences used (described in detail hereinbelow), and may be readily determined by the skilled practitioner, but the temperature should be sufficiently high or low as to be conducive to the growth of cells transformed with and expressing the temperature sensitive marker protein, but is not conducive to the growth of the non-transformed cells. For instance, for use with heat shock protein or heat shock transcription factor markers, the culture temperature may be between 35 to 50° C., while culture temperatures when using cold regulated protein or cold regulated protein transcription factor markers may be less than about 15° C.

Although some host cell species may lack a native temperature stress response system (heat shock proteins and/or cold regulation proteins), in practice, most host cells of interest will in fact possess such native systems which are functional and could allow even the non-transformed cells to grow at the temperature extremes of the culture and thereby confuse the selection process. The process of the invention is therefore adapted to minimize the induction of any of these native proteins that could protect the non-transformed cells and enable their growth at the temperature extremes used. In the preferred embodiment, after the transformation the population of cells, which will include a mix of both successfully transformed cells and non-transformed cells, is subjected to an initial culture on a growth medium under relatively normal conditions, that is, at a temperature suitable to promote the growth of all of the cells but which will not induce the expression of the host cell's native protective heat shock proteins or cold regulation proteins. However, at the same time, the expression of the temperature sensitive marker protein encoded by the nucleic acid sequence of the DNA construct by the successfully transformed cells may be effected, either by use of a operably linked constitutive promoter in the DNA construct, or by use of an inducible promoter in combination with the corresponding inducing agent in the culture. This initial culture should be continued for a period of time effective to allow an accumulation of the expressed temperature sensitive marker protein in the transformed cells to a level that will protect the cells and/or allow their growth when exposed to a subsequent extreme temperature. The timing of this pre-incubation is empirically determined for each specific host and marker construct.

Following the initial culture, the cell population is cultured at an extreme temperature, either in the same culture medium or optionally in fresh culture medium, at an extreme temperature which is effective to prevent or significantly suppress the growth of any non-transformed cells, while growth of the successfully transformed cells is supported or promoted due to the presence of the temperature sensitive marker protein expressed therein. Again, the growth medium may be liquid or solid phase, although use of solid phase media is preferred for ease of distinguishing between cells. Again, the precise temperature and culture conditions will vary with the particular host cell, temperature sensitive marker protein, and gene expression control sequences used (described in detail hereinbelow), and may be readily determined by the skilled practitioner. The same temperature extremes described above for use in selecting successful transformants from non-transformed cells lacking a functional temperature stress response system at the selected temperature may be used in this embodiment as well. However, in the preferred embodiment, the temperature is selected which is lethal to the non-transformed cells. Thus, without being limited thereto, preferred extreme culture temperatures for use with heat shock protein or heat shock transcription factor markers may be between about 40 to 50° C., particularly between about 45 to 50° C., while preferred culture temperatures when using cold regulated protein or cold regulated protein transcription factor markers may be less than about 10° C., particularly less than about 5° C. Moreover, the change in the temperature from the initial culture to the extreme temperature is applied rapidly to minimize any induction of the native temperature stress response by the non-transformed cells which might assist their survival. In a particularly preferred embodiment, the cells in the initial culture are therefore transferred to a fresh culture medium and transferred to an culture environment preheated or precooled to approximately the desired extreme temperature.

Culture at the extreme temperature should be continued for a sufficient time to allow the successfully transformed cells to grow to a sufficient level that they may be differentiated from the non-transformed cells, or until the non-transformed cells have been killed. The precise time will vary and may be readily determined by routine experimentation.

Following propagation at the extreme temperature, those cells which either exhibit significantly greater growth as evidenced by size or the production of growth products, or which survive when using temperature extremes which are lethal to non-transformed cells, are considered as presumptive positive transformants and may be isolated and recovered for further use. Plants or plant tissue may also be regenerated from transformed plant cells following their recovery.

The invention can be used for the transformation of any host cell of interest with any native or foreign or heterologous nucleic acid sequence, preferably DNA sequences. These sequences may be of any composition or function, they may encode proteins, polypeptides, regulatory elements, promoters, markers, and other non-protein producing DNA, or RNA of interest from eukaryotic or prokaryotic sources or from viruses. Without being limited thereto, DNA sequences which may be incorporated into vectors for use herein may encode intracellular proteins, membrane proteins, and/or proteins secreted into the culture medium. The DNA sequences may encode proteins of interest corresponding to all or part of native proteins found in nature. The encoded proteins may also include chimeric proteins, for example, fused polypeptides or those from mutants displaying modified biological properties. Specific examples of proteins of interest which may be encoded by the DNA sequences herein include: pharmaceuticals or veterinary agents such as cytokines, hormones, or anticoagulants, enzymes, enzyme inhibitors, and antigens or vaccines.

The DNA construct of the invention is a synthetic DNA molecule which will include one or more of the above-mentioned nucleic acid coding sequences of interest and one or more nucleic acid sequences encoding the temperature sensitive marker protein, both operatively linked to the same or different expression control sequences. In the preferred embodiment the DNA construct is a vector. The vector may contain one or more replication systems that allow it to replicate in host cells. Self-replicating vectors include plasmids, cosmids and viral vectors. Alternatively, the vector may be an integrating vector that allows the integration into the host cell's chromosome of the synthetic DNA sequence. The vector selected should also possess appropriate restriction sites for insertion of the DNA sequences of interest. A large number of vectors having polycloning sites are widely available and are suitable for use herein. Within each specific vector, various restriction sites may be generally selected for insertion of the isolated DNA sequences. Alternatively, specific restriction sites of interest may be inserted into a vector for subsequent cloning or expression of the DNA sequences of interest, using known techniques such as described by Kleid et al. (U.S. Pat. No. 5,888,808).

Vectors used in practicing the present invention are selected to be operable as cloning vectors or expression vectors in the selected host cell. While plasmid vectors are preferred, the vector may, for example, be a virus, retrovirus, bacteriophage, cosmid, artificial chromosome (bacterial or yeast), or any nucleic acid sequence that is able to replicate in a host cell. Numerous vectors, including plasmids, are known to practitioners skilled in the art, and selection of an appropriate vector and host cell is a matter of choice. A number of procaryotic plasmid expression vectors are described in U.S. Pat. Nos. 4,652,525, 4,440,859, 4,436,815, and 4,342,832, and a number of eukaryotic plasmid expression vectors have also been described in U.S. Pat. Nos. 4,546,082, 4,510,245, 4,446,235, and 4,443,540. Further, the vectors may be non-fusion vectors (i.e., those producing polypeptides of the invention not fused to any heterologous polypeptide), or alternatively, fusion vectors (i.e., those producing the polypeptide fused to a vector encoded polypeptide). The fusion proteins would, of course, vary with the particular vector chosen. Suitable non-fusion plasmid vectors for use with *E. coli* include but are not limited to pTrc99 for use with *E. coli* JM 105, or pANK-12, pANH-1 or pPL2 for use with *E. coli* MZ 1. Conversely, suitable fusion plasmid vectors include pGEX and pMC1871 for use with *E. coli* JM 105, pMAL with *E. coli* PR 722, pVB2 with *E. coli* LA5709, pTrcHis with *E. coli* INV F', pCO5 with *E. coli* N6405, and pRIT2T or PEZZ 18 with *E. coli* N4830–1. Other, non-*E. coli* expression systems which may also be employed include pAc360 or pBluescript for use with SP2 or High 5 insect cells, pYesHis with the yeast *S. cerevisiae* INVSc1 or INVSc2, pLS405 with *Salmonella dublin* SL598, and pYUB12 with *Mycobacterium smegmatis* or *M. bovis*. Still other suitable plasmid vector-host combinations that may be used in practicing the instant invention are described, for example, in U.S. Pat. Nos. 5,122,471 and 5,670,339 the contents of each of which are incorporated by reference herein.

The DNA sequences of the invention may be inserted into the desired vector by known techniques. If the vector is to serve as an expression vector, it should have or be provided with a promoter, and the DNA sequences should be inserted in the vector downstream of the promoter and operably associated or linked therewith. The promoter should be operable in the host cell into which it is to be inserted and show transcriptional activity therein (that is, the promoter should be recognized by the RNA polymerase of the host cell). While control sequences may be present with or ligated to the DNA coding sequence(s) prior to insertion into the vector, alternatively, a vector may be selected which already possesses an operable promoter. In addition, the vector may optionally have a region which codes for a ribosome binding site positioned between the promoter and the site at which the DNA sequence is inserted so as to be operably associated with the DNA sequence of the invention once inserted (in correct translational reading frame therewith). Moreover, the vector should preferably be selected to provide a region which codes for a ribosomal binding site recognized by the ribosomes of the host cell into which the vector is to be inserted. The vector may also optionally contain other regulatory sequences such as enhancer sequences, polyadenylation signals, transcription termination signals, or regulatory domains for effecting transcription and translation of the inserted coding sequences, or selectable markers as are known in the art, such as antibiotic resistance. The various DNA sequences of interest may be inserted with separate control elements, or under the control of a single promoter. The former is generally preferred when transforming eukaryotic host cells.

The promoter operatively associated with the nucleic acid sequence encoding the temperature sensitive marker protein may be naturally-occurring, composed of portions of various naturally-occurring promoters, or partially or totally synthetic. The promoter may also be inducible or constitutive, although constitutive promoters are generally preferred. If an inducible promoter is used, the selection thereof is not critical except that the temperature inducible promoters are generally not suitable for use herein. Use of such a temperature sensitive promoter would require incubation at the appropriate inducing temperature during the above-mentioned initial culture stage of the selection process, and could have the undesirable effect of stimulating the induction of the native temperature stress response systems in any non-transformed cells.

Many promoters have been described and are suitable for use herein. Without being limited thereto, suitable constitutive promoters for use in plants include: the promoters from plant viruses, such as the peanut chlorotic streak caulimovirus (PClSV) promoter (U.S. Pat. No. 5,850,019), the 35S promoter from cauliflower mosaic virus (CaMV) (Odell et al., 1985, *Nature,* 313:810–812), promoters of Chlorella virus methyltransferase genes (U.S. Pat. No. 5,563,328), and the full-length transcript promoter from figwort mosaic virus (FMV) (U.S. Pat. No. 5,378,619); the promoters from such genes as rice actin (McElroy et al., 1990, *Plant Cell*, 2:163–171), ubiquitin (Christensen et al., 1989, *Plant Mol. Biol.*, 12:619–632 and Christensen et al., 1992, *Plant Mol. Biol.*, 18:675–689), pEMU (Last et al., 1991, *Theor. Appl. Genet.*, 81:581–588), MAS (Velten et al., 1984, *EMBO J.*, 3:2723–2730), maize H3 histone (Lepetit et al., 1992, *Mol. Gen. Genet.*, 231:276–285 and Atanassova et al., 1992, *Plant Journal*, 2(3):291–300), *Brassica napus* ALS3 (PCT application WO 97/41228); and promoters of various *Agrobacterium* genes (see U.S. Pat. Nos. 4,771,002, 5,102,796, 5,182,200, 5,428,147).

Suitable inducible promoters for use in plants include but are not limited to: the promoter from the ACE1 system which responds to copper (Mett et al., 1993, *PNAS*, 90:4567–4571); the promoter of the maize In2 gene which responds to benzenesulfonamide herbicide safeners (Hershey et al., 1991, *Mol. Gen. Genetics*, 227:229–237, and Gatz et al., 1994, *Mol. Gen. Genetics*, 243:32–38), and the promoter of the Tet repressor from Tn10 (Gatz et al., 1991, *Mol. Gen. Genet.*, 227:229–237). A particularly preferred inducible promoter for use in plants is one that responds to an inducing agent to which plants do not normally respond. An exemplary inducible promoter of this type is the inducible promoter from a steroid hormone gene, the transcriptional activity of which is induced by a glucocorticosteroid hormone (Schena et al., 1991, *Proc. Natl. Acad. Sci. USA*, 88:10421) or the recent application of a chimeric transcription activator, XVE, for use in an estrogen receptor-based inducible plant expression system activated by estradiol (Zuo et al., 2000, *The Plant Journal*, 24:265–273). Other inducible promoters for use in plants are described in EP 332104, PCT WO 93/21334 and PCT WO 97/06269.

As noted hereinabove, promoters composed of portions of other promoters and partially or totally synthetic promoters can be used. See, e.g., Ni et al., 1995, *Plant J.*, 7:661–676) and PCT WO 95/14098 describing such promoters for use in plants.

The promoter may include, or be modified to include, one or more enhancer elements. Preferably, the promoter will include a plurality of enhancer elements. Promoters containing enhancer elements provide for higher levels of transcription as compared to promoters that do not include them. Suitable enhancer elements for use in plants include the PClSV enhancer element (U.S. Pat. No. 5,850,019), the CaMV 35S enhancer element (U.S. Pat. Nos. 5,106,739 and 5,164,316) and the FMV enhancer element (Maiti et al., 1997, *Transgenic Res.*, 6:143–156). See also PCT WO 96/23898 and *Enhancers And Eukaryotic Expression* (Cold Spring Harbor Press, Cold Spring Harbor, N.Y., 1983).

For efficient expression, the coding sequences are preferably also operatively linked to a 3' untranslated sequence. The 3' untranslated sequence will include a transcription termination sequence and a polyadenylation sequence. The 3' untranslated region can be obtained from the flanking regions of genes from *Agrobacterium*, plant viruses, plants or other eukaryotes. Suitable 3' untranslated sequences for use in plants include those of the cauliflower mosaic virus 35S gene, the phaseolin seed storage protein gene, the pea ribulose biphosphate carboxylase small subunit E9 gene, the soybean 7S storage protein genes, the octopine synthase gene, and the nopaline synthase gene.

A 5' untranslated sequence is also employed. The 5' untranslated sequence is the portion of an mRNA which extends from the 5' CAP site to the translation initiation codon. This region of the mRNA is necessary for translation initiation in plants and plays a role in the regulation of gene expression. Suitable 5' untranslated regions for use in plants include those of alfalfa mosaic virus, cucumber mosaic virus coat protein gene, and tobacco mosaic virus.

In general, after construction of a suitable expression vector, the vector is transformed into the host cell of interest. Depending on the host cell used, transformation is performed using standard techniques. For example, the calcium treatment employing calcium chloride, described by Cohen (1972, *Proc. Natl. Acad. Sci. USA*, 69:2110), or the RbC1 method, described in Sambrook et al., (ibid) may be used for prokaryotes or other cells which contain substantial cell wall barriers. Infection with *Agrobacterium tumefaciens* such as described by Shaw (1983, Gene, 23:315) may be used for certain plant cells. For mammalian cells without such cell walls, the calcium phosphate precipitation method of Graham and Van der Eb (1978, *Virology*, 52:546), or electroporation described in Sambrook et al. (ibid), may be used. Transformations into yeast may be conducted, for example, according to the method of Van Solingen, et al. (1977, *J. Bacter.*, 130:946), and Hsiao et al. (1979, *Proc. Natl. Acad. Sci. USA*, 76:3829).

Use of the invention is particularly preferred for the transformation of plant cells and selecting those plant cells which have been successfully transformed. Methods of transforming plant cells are well known in the art. For instance, numerous methods for plant transformation have been developed, including biological and physical transformation protocols. See, for example, Miki et al., "Procedures for Introducing Foreign DNA into Plants" in *Methods in Plant Molecular Biology and Biotechnology*, B. R. Glick and J. E. Thompson, Eds. (CRC Press, Inc., Boca Raton, Fla., 1993) pp. 67–88. In addition, vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, Fla., 1993) pp. 89–119.

The most widely utilized mechanism for introducing an expression vector into plants is based on the natural transformation systems of *Agrobacterium*. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, 1991, C.I., *Crit. Rev. Plant. Sci.*, 10:1. Descriptions of *Agrobacterium* vector systems and methods for *Agrobacterium*-mediated gene transfer are provided by numerous references. See, for example, Horsch et al., 1985, *Science*, 227:1229, Hoekema et al., 1983, *Nature*, 303:179, de Framond et al., 1983, *Bio/Technology*, 1:262, Jordan et al., 1988, *Plant Cell Reports*, 7:281–284, Leple et al., 1992, *Plant Cell Reports*, 11:137–141, Stomp et al., 1990, *Plant Physiol.*, 92:1226–1232, Knauf et al., 1982, *Plasmid*, 8:45–54), Gruber et al. (ibid), Miki et al. (ibid), Moloney et al., 1989, *Plant Cell Reports*, 8:238, PCT applications WO 84/02913, WO 84/02919 and WO 84/02920, EP 116,718, and U.S. Pat. Nos. 4,940,838, 5,464,763, and 5,929,300.

A generally applicable method of plant transformation is microprojectile-mediated transformation wherein DNA is carried on the surface of microprojectiles. The expression vector is introduced into plant tissues with a biolistic device that accelerates the microprojectiles to speeds sufficient to penetrate plant cell walls and membranes. Sanford et al., 1987, *Part. Sci. Technol.*, 5:27, Sanford, 1988, *Trends Biotech.*, 6:299, Sanford, 1990, *Physiol. Plant*, 79:206, Klein et al., 1992, *Biotechnology*, 10:268, Klein et al., 1987, *Nature*, 327:70–73.

Another method for physical delivery of DNA to plants is sonication of target cells. Zhang et al., 1991, Bio/Technology, 9:996. Alternatively, liposome or spheroplast fusion have been used to introduce expression vectors into plants. Deshayes et al., 1985, EMBO J., 4:2731, Christou et al., 1987, Proc. Natl. Acad. Sci. USA, 84:3962. Direct uptake of DNA into protoplasts using $CaCl_2$ precipitation, polyvinyl alcohol or poly-L-ornithine have also been reported. Hain et al., 1985, Mol. Gen. Genet., 199:161 and Draper et al., 1982, Plant Cell Physiol., 23:451. Electroporation of protoplasts and whole cells and tissues have also been described. Donn et al., In Abstracts of VIIth International Congress on Plant Cell and Tissue Culture IAPTC, A2-38, p. 53 (1990); D'Halluin et al., 1992, Plant Cell, 4:1495–1505, Spencer et al., 1994, Plant Mol. Biol., 24:51–61, and Fromm et al., 1985, Proc. Natl. Acad. Sci. USA, 82:5824. Other techniques include microinjection (Crossway, 1985, Mol. Gen. Genetics, 202:179–185), polyethylene glycol transformation (Krens et al., 1982, Nature, 296:72–74), fusion of protoplasts with other entities, either minicells, cells, lysosomes, or other fusible lipid-surfaced bodies (Fraley et al., 1982, Proc. Natl. Acad. Sci. USA, 79:1859–1863), and techniques set forth in U.S. Pat. No. 5,231,019).

After transformation, the successfully transformed cells may be selected using the process of the invention described hereinabove. Successfully transformed colonies are then recovered and cultured in order to produce the proteins or polypeptides encoded by the nucleic acid coding sequences of the DNA construct, or to produce cells having a well-defined number of copies of the DNA constructs. In the preferred embodiment for transformation of plant cells, after selection, transformed plant cells may be regenerated into transgenic plants. Plant regeneration techniques are well known in the art and include those set forth in the Handbook of Plant Cell Culture, Volumes 1–3, Evans et al., eds. Macmillan Publishing Co., New York, N.Y. (1983, 1984, 1984, respectively); Predieri and Malavasi, 1989, Plant Cell, Tissue, and Organ Culture, 17:133–142; James et al., 1988, J. Plant Physiol., 132:148–154; Fasolo et al., 1989, Plant Cell, Tissue, and Organ Culture, 16:75–87; Valobra and James, 1990, Plant Cell, Tissue, and Organ Culture, 21:51–54; Srivastava et al., 1985, Plant Science, 42:209–214; Rowland and Ogden, 1992, Hort. Science, 27:1127–1129; Park and Son, 1988, Plant Cell, Tissue, and Organ Culture, 15:95–105; Noh and Minocha, 1988, Plant Cell Reports, 5:464–467; Brand and Lineberger, Plant Science, 57:173–179 (1988); Bozhkov et al., 1992, Plant Cell Reports, 11:386–389; Kvaalen and von Arnold, 1991, Plant Cell, Tissue, and Organ Culture, 27:49–57; Tremblay and Tremblay, 1991, Plant Cell Tissue, and Organ Culture, 27:95–103; Gupta and Pullman, U.S. Pat. No. 5,036,007; Michler and Bauer, 1991, Plant Science, 77:111–118; Wetzstein et al., 1989, Plant Science, 64:193–201; McGranahan et al., 1988, Bio/Technology, 6:800–804; Gingas, 1991, Hort. Science, 26:1217–1218; Chalupa, 1990, Plant Cell Reports, 9:398–401; Gingas and Lineberger, 1989, Plant Cell, Tissue, and Organ Culture, 17:191–203; Bureno et al., 1992, Phys. Plant., 85:30–34; and Roberts et al., 1990, Can. J. Bot., 68:1086–1090.

A variety of host cells may be transformed and selected using the process of the invention. Host cells may be either prokaryotic or eukaryotic, and when the host cells are bacterial cells, they may be either gram-negative or gram-positive bacteria. Strains of Escherichia coli are generally preferred for use in prokaryotic systems. However, without being limited thereto, other useful hosts include species of Salmonella (including, for example, S. typhimurium, S. enteriditis, and S. dublin) species of Mycobacterium (such as M. smegmatis and M. bovis, species of Pseudomonas (including, for example, P. aeruginosa and P. putida), Bacillus subtilis, yeasts and other fungi (for example, Saccharomyces cerevisiae), plant cells such as plant cells in culture (including, for example, P. aeruginosa and P. putida), Bacillus subtilis, yeasts and other fungi (for example, Saccharomyces cerevisiae), plant cells such as plant cells in culture (including, for example, both angiosperms and gymnosperms) and animal cells such as animal cells in culture. Non-limiting examples of transgenic plants which may be produced and selected according to the invention include, species from the genera Fragaria, Lotus, Medicago, onobrychis, Trifolium, Trigonella, Vigna, Citrus, Linum, Ceranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Bromus, Asparagus, Antirrhinum, Hererocallis, Nemesia, Pelargonium, Panicum, Pennisetum, Ranunculus, Sencia, Salpiglossis, Cucumis, Browalia, Glycine, Lolium, Zea, Triticum, Sorghum, Malus, Apium, Datura and woody dicotyledonous forest tree species, and particularly, corn, sorghum, small grains, sugarcane, asparagus, grasses, and broadleaf plants, including beans, soybeans, cotton, peas, potatoes, sunflowers, tomatoes, tobacco, fruit trees, ornamental plants, trees.

The following examples are intended only to further illustrate the invention and are not intended to limit the scope of the invention, which is defined by the claims.

EXAMPLE 1

In this example, the use of the invention for temperature selection of transgenic cells within cell suspension cultures was investigated. In summary, a gene reported to play a crucial role in thermotolerance (Queitsch et al., 2000, The Plant Cell, 12:479–492) encoding the Arabidopsis thaliana heat shock protein 101 was placed under the control of the constitutive ocs/mas 'superpromoter', incorporated into an expression vector and transferred into cotton hypocotyls cells via Agrobacterium. The callus that developed was a mixture of transformed and non-transformed cells as there was no selection pressure applied during callus development. The callus was moved to cell suspension medium and the cell suspension was allowed to grow for 9 days. The cell suspension flasks were than transferred to a 50° C. water bath for enrichment of transgenic cells and embryos.

The binary expression vector, pE1801-ocs/mas 'superpromoter'-HSP101 plasmid, containing the Arabidopsis thaliana heat shock protein 101 under the control of the constitutive ocs/mas 'superpromoter' was used in this example. In this vector, which is shown in FIG. 1, PAg7= Transcription termination and poly-Adenylation signal sequence from Octopine Ti-Plasmid T-DNA (gene for transcript #7) (Velten and Schell, 1985, Nucleic Acids Res., 13:6981–6998). NptII=Neomycin phosphotransferase II coding region (Fraley et al., 1983, Proc. Natl. Acad. Sci. USA, 80:4803–4807). Pnos=Nopaline synthase promoter from Nopaline Ti-Plasmid T-DNA (Koncz et al., 1983, EMBO J., 2(9): 1597–1603). Aocsx3=Octopine synthase enhancer element (3 copies) from Octopine T-Plasmid T-DNA (Bouchez et al., Dec. 20, 1989, EMBO J., 8(13) :4197–4204). AmasPmas=Manopine synthase promoter from Octopine Ti-Plasmid T-DNA (Velten et al., 1984, EMBO J., 3:2723–2730). HSP101=Heat shock protein (101 kdalton molecular weight) from A. thaliana (Queitsch et al., 2000, *The Plant Cell*, 12:479–492). Ags-ter=Transcription termination and poly-Adenylation signal sequence from Octopine Ti-Plasmid T-DNA (Agropine synthase gene) (Bandyopadhyay et al., Nov. 15, 1989, *J. Biol. Chem.*, 264(32):19399–19406). The contents of each of the references referred to above are incorporated by reference herein.

Figure 2:
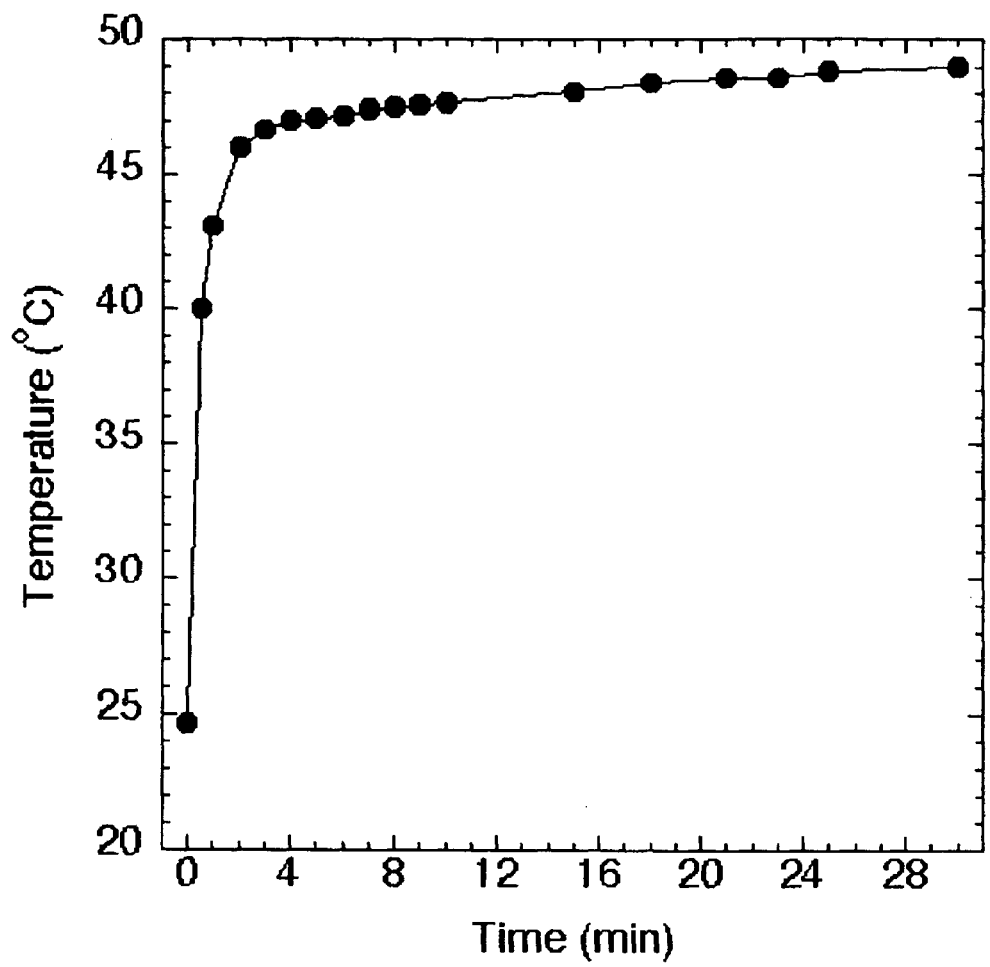
FIG. 2: Graph of the time course of temperature increases in the cell suspension cultures in a 50° C. water bath.

The pE1801-ocs/mas 'superpromoter'-HSP101 plasmid was introduced into EHA 105 strain of *Agrobacterium tumefacians* (Hood et al., 1993, *Transgenic Research*, 2:208–218) by direct transformation as described by Walker-Peach and Velten, in Plant Molecular Biology Manual, section B1:1–19 (Gelvin, Shilperoot and Verma, eds., Kluwer Academic Publishers, Dordrecht, The Netherlands, 1994, the contents of which are incorporated by reference herein). The constructs were subsequently introduced by *Agrobacterium* transfection into hypocotyls explants, by cutting submerged hypocotyls in a 24-hour-old culture of EHA 105, containing the appropriate construct, grown at 28° C. The hypocotyls sections were blotted dry on sterile filter paper to remove excess EHA 105, and transferred onto T2 Media (4.4 g/L MS medium with Gamborg's vitamins+0.1 mg/L 2,4-D and 0.5 mg/L kinetin+30 g/L D-(+)-glucose+2 g/L phytagel). The infected hypocotyl tissue was incubated on T2 medium at 28° C. for 2 days prior to transfer to MS2NK CL medium (4.4 g/L MS medium with Gamborg's vitamins+2 g/L phytagel+30 g/L D-(+)-glucose+2 mg/L alpha-naphthaleneacetic acid+0.1 mg/L kinetin+266 mg/L cefotaxime). Hypocotyls were transferred to fresh MS2NK CL medium three weeks following *Agrobacterium* infection. Four weeks after the transfer, cali were cut from the hypocotyls ends and moved onto MS2NK 1/4 CL medium (4.4 g/L MS medium with Gamborg's vitamins+2 g/L phytagel+30 g/L D-(+)-glucose+2 mg/L alpha-naphthaleneacetic acid+0.1 mg/L kinetin+67 mg/L cefotaxime). Six to seven weeks following the transfer to MS2NK 1/4 CL medium the calli were moved into MSNH cell suspension medium (4.4 g/L MS medium with Gamborg's vitamins+30 g/L D-(+)-glucose) and placed on a rotary shaker at 110 rpm. After 9 days on the shaker, cell suspensions were transferred to a 50° C. water bath with shaker set to 110 rpm. The time course of temperature change in the cell suspension medium is shown in FIG. 2. Treatments of 5, 10, 16, 18, 21, 25 and 30 minutes were evaluated. No embryos were recovered from the 25 or 30 minute incubations. Two embryos were recovered from a cell suspension culture incubated for 21 minutes. Embryo survival increased with decreasing time of exposure. Although screening for transgenics in cell suspensions was feasible, it was not practical as cultures had to be quickly centrifuged and resuspended in room temperature MSNH media prior to plating on MSK medium (4.4 g/L MS medium with Gamborg's vitamins+30 g/L D-(+)-glucose+1.9 g/L KNO$_3$+2 g/L phytagel).

EXAMPLE 2

In this second example, the use of the invention for temperature selection of transgenic cells on a solid medium was investigated. Briefly, the binary expression vector containing the *Arabidopsis thaliana* heat shock protein 101 was transferred into cotton hypocotyls, and callus was developed therefrom as in Example 1. The callus, which was a mixture of transformed and non-transformed cells was moved to cell suspension medium and the cell suspension was allowed to grow for 9 days. The cells and embryos were then transferred to a solid medium followed by exposure to elevated temperatures in a 50° C. incubator for selection of transgenic cells and embryos.

Figure 3:
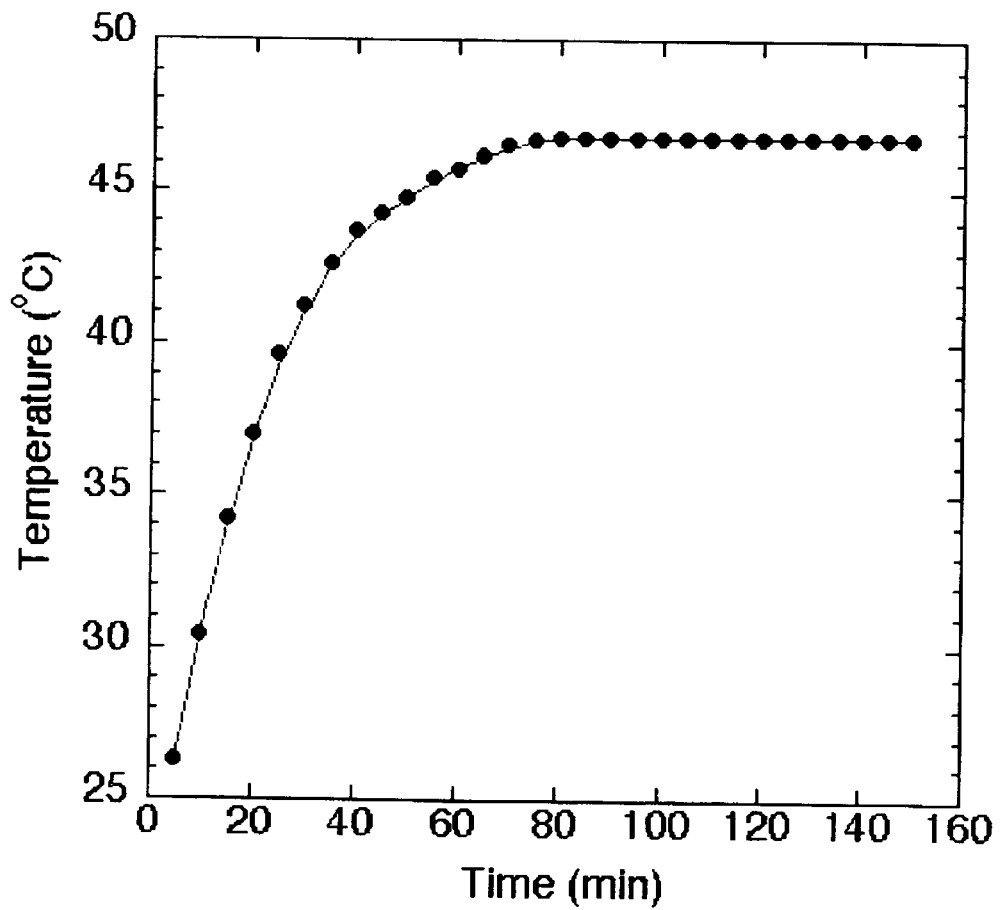
FIG. 3: Graph of the time course of temperature increases in the solid medium during selection in a 50° C. incubator.

As described in Example 1, the binary vector pE1801-ocs/mas 'superpromoter'-HSP101 was introduced *Agrobacterium tumefacians*, hypocotyl explants were transfected therewith, transferred onto T2 Media and incubated, transferred to MS2NK CL medium, calli were cut from the hypocotyl's ends and moved onto MS2NK 1/4 CL medium, and calli were moved into MSNH cell suspension medium and placed on a rotary shaker. After 9 days on the shaker, cell suspensions were transferred to MSK medium (4.4 g/L MS medium with Gamborg's vitamins+30 g/L D-(+)-glucose+1.9 g/L KNO$_3$+2 g/L phytagel). Immediately upon transfer of the embryogenic cell suspensions to MSK plates, one half of the MSK plates per cell suspension were placed in a 50° C. incubator for 150 minutes while the other half of the plates were held at 28° C. Petri dishes were stacked 5 plates high on each of 3 shelves within the incubator. A thermocouple was added to MSK medium that did not receive a cell suspension and this reference plate was placed on the middle shelf in the middle of the stack of the MSK plates in the 50° C. incubator. Phytagel surface temperature was measured every 5 minutes throughout the 150 minute incubation (FIG. 3). Following the heat treatment, the Petri dishes were moved to a 28° C. tissue culture room and embryo development followed over a 9-day period. Seventy-one plates out of the 172 plates that were heat-treated developed 1 or more embryos. Fifteen plates were chosen at random from the seventy-one and analyzed for the presence of the introduced HSP101 gene. Six plates had PCR-positive embryos for a total of 16 transgenic embryos out of the 50 embryos evaluated. This translates to a 32% efficiency in recovery of transgenic embryos. We then evaluated the effectiveness of the heat treatment on reducing embryo development in 13 of the 15 samples. The two remaining samples failed to provide untreated controls because of plate contamination. In samples 2, 7, 10, 11, and 13, the heat treatment was ineffective in reducing the number of embryos compared with the nontreated controls. These samples accounted for 21 of the 50 embryos harvested from these plates. By eliminating plates that fail to show reduced embryo numbers following heat treatment, the efficiency of recovery of transgenic embryos increases to 55%.

| Plate Number | Total Number of Embryos | Number Transformed | Treated/Nontreated Embryos |
|---|---|---|---|
| 1 | 1 | 0 | — |
| 2 | 1 | 0 | 1/1 |
| 3 | 1 | 0 | 1/10 |
| 4 | 1 | 1 | 1/3 |
| 5 | 1 | 1 | 1/6 |
| 6 | 3 | 0 | 3/9 |
| 7 | 3 | 0 | 3/3 |
| 8 | 4 | 1 | 4/8 |
| 9 | 3 | 0 | 3/7 |
| 10 | 5 | 0 | 5/5 |
| 11 | 5 | 0 | 7/8 |
| 12 | 6 | 6 | 6/14 |
| 13 | 7 | 0 | 29/10 |
| 14 | 5 | 4 | — |
| 15 | 4 | 3 | 4/10 |
| Total | 50 | 16 | |

EXAMPLE 3

In the third example, the use of the invention for the temperature selection of transgenic plants was investigated. In brief, the binary expression vector containing the *Arabidopsis thaliana* heat shock protein 101 was transferred into tobacco leaf disks via *Agrobacterium*. Transgenic plants were selected on kanamycin, selfed, and the segregating population of R1 seedlings evaluated for enhanced heat resistance via a modification of a hypocotyl elongation assay described by Hong and Vierling (2000, PNAS, 97:4392–4397).

The binary vector pE1801-ocs/mas 'superpromoter'-HSP101 was introduced into *Agrobacterium tumefacians* as described in Example 1. The *Agrobacterium* was grown, with its proper selective antibiotics, in 5 ml of LB. The newly grown bacterium was diluted 1:4 in a sterile tube containing LB broth. The solution was gently agitated until the bacteria became suspended in the LB. A turgid tobacco leaf was sterilized for 8 minutes in a 20% Sodium Hypo chlorite (generic bleach 5.25% by weight) and 0.1% SDS solution followed by treatment in 70% ethanol. Leaf punches were dropped into an MSIO (0.44% Murashige/Skoog basal salts, 3% Sucrose, 0.1 ug/ml naphtaleneacetic acid, and 1.0 ug/ml benzilaminopurine) petri plate. The contents of the inoculum were poured into the petri plate containing the explants. The explants were co-incubate with the bacterium for 24 hours at 28° C. with a 16/8 hour light cycle.

The leaf disks were transferred into a MS10 plate supplemented with Kanamycin (150 mg/L)+Carbenicillin (500 mg/L). Leaf disks were transferred onto fresh plates of MS10 Kanamycin (150 mg/L)+Carbenicillin (500 mg/L) at 2 week intervals. When callus began to grow, excess portions of the tumorous mass were removed. When the callus mass differentiated into a visible shoot with at least four well formed leaves and a 3 mm stem it was excised and transferred to rooting media. This media consists of the basic ingredients of the regeneration media but without BAP as the active hormone. Selection for the transformants was still maintained by Kanamycin at 150 mg/L and 350 mg/L Carbenicillin for the *Agro* strain. Once the regenerants had a well-developed root system, they were transferred to sterile soil and placed in an aquarium containing water plus a plant food additive with a clear top to allow humidity to accumulate to a high level.

Twenty-four R0 plants were isolated and four were identified by antibody analyses as expressing high levels of HSP101. Selected plants were selfed and the R1 seeds collected for analysis of heat tolerance. R1 seeds were placed on 1% Phytagar medium, the Petri dishes were place vertically in the dark in a 23° C. incubator for 5 days. Seedlings of equal size were transferred to 1% agarose medium and the petri dish bottom was positioned on moist 3 MM filter paper on the temperature blocks of an electronically controlled eight-position thermal plate system termed "CELTEC" (Burke and Mahan 1993). The seedlings were challenged at 50° C. for 5 minutes and then returned to the 23° C. incubator for 2 days.

Hypocotyl elongation was inhibited in control seedlings and two of the seedlings in the HSP101 R1 sample. Seven of the nine HSP101 R1 seedlings exhibited continued hypocotyl elongation following heat treatment consistent with genetic expected segregation patterns. In the first experiment, two of the four seedlings exhibited continued hypocotyls elongation following heat treatment and in the second experiment four of the five seedlings exhibited continued hypocotyls elongation following heat treatment. PCR analysis of the seedlings showed that HSP101 was present only in the seedlings that exhibited continued hypocotyls elongation following heat treatment thereby supporting it's use as a selection tool for identifying transgenic plants containing the introduced Arabidopsis HSP101.

It is understood that the foregoing detailed description is given merely by way of illustration and that modifications and deviations may be made therein without departing from the spirit and scope of the invention.

We claim:

1. A method for selecting a cell transformed with one or more nucleic acid coding sequences comprising:
   (a) transforming a population of cells with a foreign DNA construct comprising at least one first nucleic acid coding sequence and a second nucleic acid coding sequence encoding a temperature sensitive marker protein selected from the group consisting of heat shock proteins, heat shock transcription factors, cold regulated proteins, and cold regulated protein transcription factors, each of said first and second nucleic acid coding sequences being operatively linked to gene expression control sequences, said transforming generating a second population of cells comprising cells which have been successfully transformed with said foreign DNA construct and non-transformed cells,
   (b) selecting said cells which have been successfully transformed from said non-transformed cells in said second population of cells from said transforming in (a), said selecting consisting essentially of culturing said second population of cells under temperature conditions wherein growth of said non-transformed cells is suppressed or prevented while growth of said cells which have been successfully transformed is supported, and
   (c) recovering cells from (b) exhibiting significant growth, wherein the recovered cells exhibiting significant growth are said cells which have been successfully transformed.

2. The method of claim 1 further comprising, prior to said selecting, propagating said second population from said transforming in (a) under conditions effective to promote expression of said temperature sensitive marker protein by said cells which have been successfully transformed.

3. The method of claim 2 wherein said propagating is at a temperature which is not effective to induce a heat shock response in said second population of cells.

4. The method of claim 1 wherein said cells are selected from the group consisting of plant cells, animal cells, and microorganisms.

5. The method of claim 4 wherein said cells are microorganisms and said microorganisms are selected from the group consisting of bacterial cells, tungal cells, and yeast cells.

6. The method of claim 4 wherein said cells are plant cells and said gene expression control sequences are plant gene expression control sequences.

7. The method of claim 6 further comprising generating a plant from one of said plant cells transformed with said DNA construct.

8. The method of claim 1 wherein said first and second nucleic acid coding sequences are operatively linked to the same gene expression control sequence.

9. The method of claim 1 wherein said first and second nucleic acid coding sequences are operatively linked to different gene expression control sequences.

10. The method of claim 1 wherein said temperature sensitive marker protein is a heat shock protein.

11. The method of claim 10 wherein said heat shock protein is selected from the group consisting of the families of HSP 100, HSP 90, HSP 70, HSP 60, and low molecular weight HSPs.

12. The method of claim 11 wherein said heat shock protein is from the family of HSP 100.

13. The method of claim 1 wherein said temperature sensitive marker protein is a heat shock protein or a heat shock transcription factor and said temperature conditions are greater than or equal to about 45° C.

14. The method of claim 1 wherein said temperature sensitive marker protein is a cold regulated protein or a cold regulated protein transcription factor and said temperature conditions are less than or equal to about 10° C.

15. The method of claim 1 wherein said temperature conditions are lethal to said non-transformed cells.

16. The method of claim 1 wherein said DNA construct does not comprise an antibiotic resistance marker or a pesticide resistance marker.

17. The method of claim 1 wherein said first nucleic acid coding sequence is heterologous to said cells.

18. The method of claim 1 wherein said DNA construct comprises a vector.

19. A method for selecting a cell transformed with one or more nucleic acid coding sequences comprising:

(a) transforming a population of cells with a foreign DNA construct comprising at least one first nucleic acid coding sequence and a second nucleic acid coding sequence encoding a temperature sensitive marker protein selected from the group consisting of heat shock proteins, heat shock transcription factors, cold regulated proteins, and cold regulated protein transcription factors, each of said first and second nucleic acid coding sequences being operatively linked to gene expression control sequences, said transforming generating a second population of cells comprising cells which have been successfully transformed with said foreign DNA construct and non-transformed cells, (b) selecting said cells which have been successfully transformed from said non-transformed cells in said second population from said transforming in (a), wherein said selecting comprises culturing said second population of cells under temperature conditions wherein growth of said non-transformed cells is suppressed or prevented while growth of said cells which have been successfully transformed is supported, and said selecting does not comprise any of: culturing said second population of cells transformed in (a) on culture media comprising an antibiotic or pesticide, or detection of toxins, enzyme products, or pigments produced by said cells, and (c) recovering cells from (b) exhibiting significant growth, wherein the recovered cells exhibiting significant growth are said cells which have been successfully transformed.

20. A method for selecting a cell transformed with one or more nucleic acid coding sequences comprising:

(a) transforming a population of cells with a foreign DNA construct comprising at least one first nucleic acid coding sequence and a second nucleic acid coding sequence encoding a temperature sensitive marker protein selected from the group consisting of heat shock proteins, heat shock transcription factors, cold regulated proteins, and cold regulated protein transcription factors, each of said first and second nucleic acid coding sequences being operatively linked to gene expression control sequences, (b) culturing said population of cells transformed in (a) under temperature conditions wherein growth of non-transformed cells is suppressed or prevented while growth of cells transformed with said DNA construct is supported, and (c) recovering cells from (b) exhibiting significant growth as presumptive positive transformants, wherein said DNA construct does not comprise an antibiotic resistance marker or a pesticide resistance marker.

* * * * *